(12) United States Patent
Ohad et al.

(10) Patent No.: US 6,350,239 B1
(45) Date of Patent: Feb. 26, 2002

(54) METHOD AND APPARATUS FOR DISTRIBUTED SOFTWARE ARCHITECTURE FOR MEDICAL DIAGNOSTIC SYSTEMS

(75) Inventors: Nimrod Ohad, Haifa; Michael Moshkovich, Naharia, both of (IL)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/473,400

(22) Filed: Dec. 28, 1999

(51) Int. Cl.$^7$ .................................. A61B 8/00
(52) U.S. Cl. ........................................ 600/437
(58) Field of Search ................... 600/437, 300, 600/407, 459, 443, 447; 395/200.32; 370/421

(56) References Cited

U.S. PATENT DOCUMENTS

| | | | |
|---|---|---|---|
| 5,415,167 A | * 5/1995 | Wilk | 600/407 |
| 5,603,323 A | * 2/1997 | Pflugrath et al. | 600/437 |
| 5,758,649 A | * 6/1998 | Iwashita et al. | 600/459 |
| 5,778,177 A | * 7/1998 | Azar | 395/200.32 |
| 5,851,186 A | * 12/1998 | Wood et al. | 600/437 |
| 5,944,659 A | * 8/1999 | Flach et al. | 600/300 |
| 6,081,533 A | * 6/2000 | Laubach et al. | 370/421 |

* cited by examiner

*Primary Examiner*—Marvin M. Lateef
*Assistant Examiner*—Ali M. Imam
(74) *Attorney, Agent, or Firm*—McAndrews, Held & Malloy, Ltd.; Peter J. Vogel; Michael A. Dellapenna

(57) ABSTRACT

A distributed medical diagnostic system is implemented using one or more first computers that execute one or more instances of a first medical diagnostic system software module and one or more second computers that execute one or more instances of a second medical diagnostic system software module. The first and second medical diagnostic system software modules are members of a system software set (including any number of such system software modules) that implements any chosen medical diagnostic system. One or more communication links are present to provide communication between the system software modules that exchange data.

34 Claims, 3 Drawing Sheets

METHOD AND APPARATUS FOR DISTRIBUTED SOFTWARE ARCHITECTURE FOR MEDICAL DIAGNOSTIC SYSTEMS

BACKGROUND OF THE INVENTION

The present invention generally relates to medical diagnostic systems, and in particular relates to distributed software configurations for medical diagnostic systems.

Sophisticated medical diagnostic systems have long been available to doctors. As examples, doctors employ ultrasound imaging systems, X-ray imaging systems, and Magnetic Resonance Imaging (MRI) on a daily basis as an aid in diagnosing illness, preventing illness, and investigating patient health concerns. As technology has progressed, medial diagnostic systems have increased in capability and complexity, and now operate primarily under control of a sophisticated computer system embedded in the medical diagnostic system.

The computer system is responsible for many tasks. Not only must the computer system operate the diagnostic system hardware itself, but the computer system must also allow access to patient records and archived data (e.g., X-ray images), process reports, perform image processing, track maintenance requests and the like. Thus, the computer system provides a single interface to many important functions necessary to operate the diagnostic system.

In the past, however, medical diagnostic system designers have implemented the computer system as a single integrated system. In other words, a computer system performs the wide variety of tasks required for the diagnostic system to operate. This approach suffers from a number of drawbacks, including, for example, the limited ability to optimize the computer system hardware for each type task the computer system must perform, the limited ability to perform hardware maintenance or software upgrades without taking the entire computer system down, and limited ability to allow multiple doctors, technicians, or support personnel to use different software modules at the same time (e.g., to allow a secretary to run a patient report while allowing a doctor to capture an X-ray image).

A need has long existed in the industry for a distributed software architecture for medical diagnostic systems that overcomes the problems noted above, and others previously experienced.

BRIEF SUMMARY OF THE INVENTION

A preferred embodiment of the present invention provides a distributed medical diagnostic system. The distributed medical diagnostic system may, for example, be implemented using a first computer that executes a first medical diagnostic system software module and a second computer, separate from the first computer, that executes a second medical diagnostic system software module. The first and second medical diagnostic system software modules are members of a system software and hardware set that implements any chosen medical diagnostic system. In other words, the hardware and software that implement a single medical diagnostic system are distributed among several computers. A communication interface is present in both the first computer and in the second computer. The first and second software modules communicate with one another through the communication interfaces.

The medical diagnostic system is preferably an ultrasound system as described in more detail below. However, as additional examples, the medical diagnostic system may also be a Magnetic Resonance Imaging (MRI) system, an X-ray imaging system, or another type of diagnostic system.

A further embodiment of the present invention provides a method for implementing a distributed medical diagnostic system. The method first separates a system software set for a chosen medical diagnostic system into software modules. Next, the method distributes the software modules among at least first and second separate computers and connects the first and second computers through communication interfaces. In addition, the method preferably connects at least one of the first and second computers to an electromechanical subsystem of the medical diagnostic system.

DETAILED DESCRIPTION OF THE INVENTION

Figure 1:
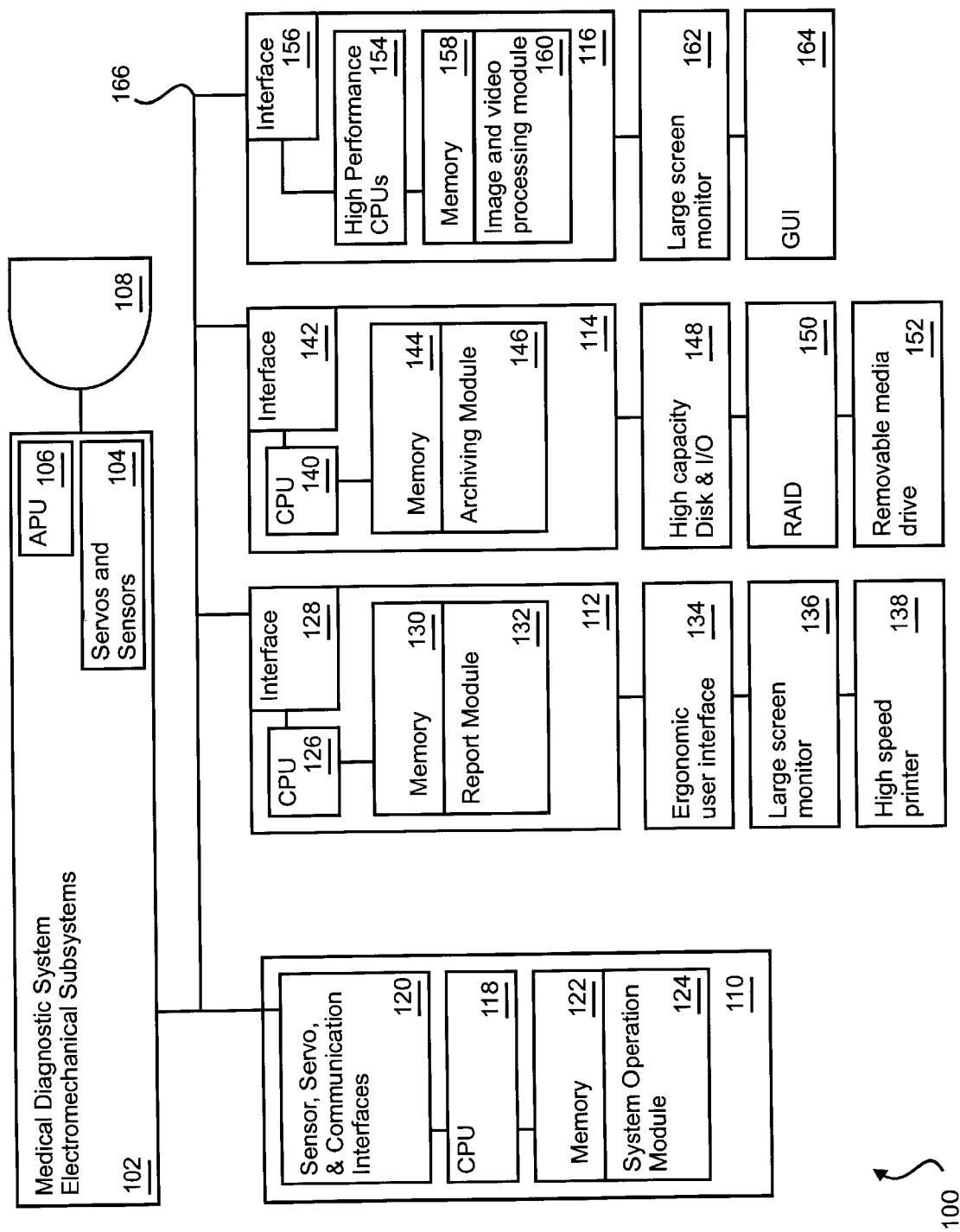
FIG. 1 illustrates one example of a distributed medical diagnostic system.

Turning first to FIG. 1, that figure shows a distributed medical diagnostic system 100. The diagnostic system 100 includes an electromechanical subsystem 102 which implements the electronic and mechanical subsystems of a diagnostic system apart from the computers that execute the software modules discussed below. The electromechanical subsystem 102, depending on the particular system implemented, may incorporate, for example, mechanical motor servos and feedback sensors 104, a magnet, X-ray image detectors, or an Acoustic Power Unit (APU) 106 coupled to an ultrasound scanner 108. In other words, the distributed diagnostic system may be implemented as any desired diagnostic system, including an MRI system, X-ray system, ultrasound system, electron microscope, heart monitor system, and the like.

Also shown in FIG. 1 are a system computer 110, a report computer 112, an archiving computer 114, and an imaging computer 116. The system computer 110 includes one or more CPUs 118 coupled to a servo/sensor and communications interface 120 and a memory 122. The memory 122 stores a system operation software module 124.

The report computer 112 similarly includes one or more CPUs 126 coupled to a communication interface 128 and a memory 130. The memory 130 stores a report software module 132. Preferably, the report computer 112 is connected to an ergonomic user interface 134, a large screen monitor 136, and a high speed printer 138.

The archiving computer 114 includes one or more CPUs 140 coupled to a communication interface 142 and a memory 144. The memory 144 stores an archiving software module 146. The archiving computer 114 may include, for example, a high capacity disk and I/O subsystem 148, a Redundant Array of Inexpensive Disks (RAID) 150, and a high capacity removable media drive 152 (e.g., a rewriteable CDROM, or, preferably, a Magneto optical disk).

The imaging computer 116 includes one or more high performance CPU subsystems 154 coupled to a communication interface 156 and a high capacity memory 158. The memory 158 stores an image and video processing software module 160. The imaging computer 116 may include, for example, a large screen, high resolution monitor 162 which displays a Graphical User Interface (GUI) 164 under control of software stored in the memory 158.

One or more communication links 166 couple together the system computer 110, the report computer 112, the archiving computer 114, and the imaging computer 116. The communication link may support any desired communication protocol, including as examples, serial (e.g. RS 232), parallel (i.e., IEEE 1284), Token Ting, TCP/IP, or ATM network protocols. The communication links 166 may be separately implemented as direct wired connections (e.g., with network cable, phone lines, or serial/parallel cable), wireless connections (e.g., infrared or RF), or a combination of the two. One of the communication links 166 also connects to the electromechanical subsystem 102 and supports communication between the software modules and the electromechanical subsystem 102. Before discussing in detail the distribution of software modules to computers that are particularly adapted to execute the software modules, the software modules are described with reference to FIG. 2.

Figure 2:
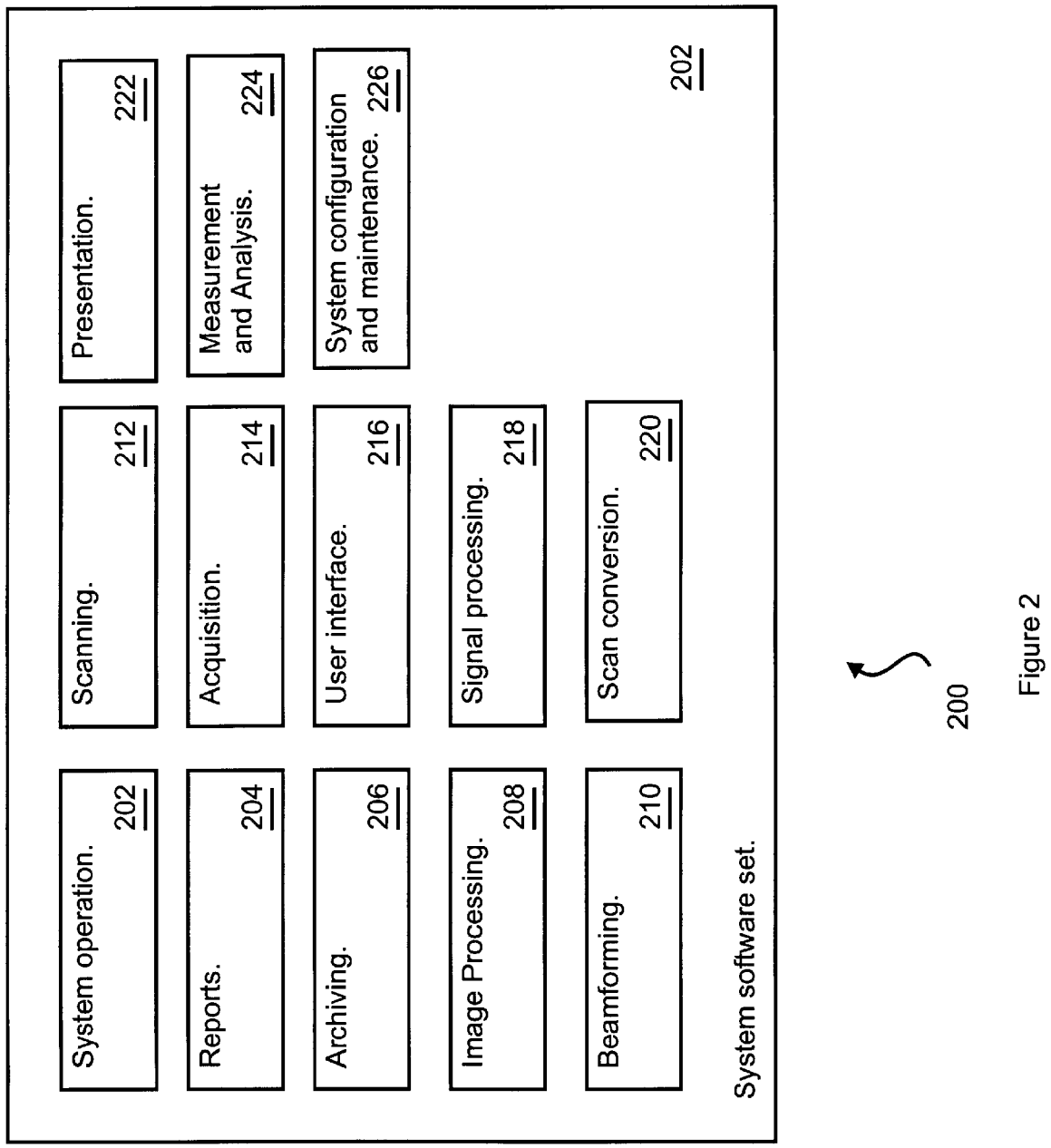
FIG. 2 shows an exemplary system software set for a medical diagnostic system.

Turning to FIG. 2, that figure shows a system software set 200. The system software set 200 includes the following software modules: system operation module 202, report module 204, archiving module 206, image processing module 208, beamforming module 210, scanning module 212, acquisition module 214, user interface module 216, signal processing module 218, scan conversion module 220, presentation module 222, measurement and analysis module 224, and a diagnostic system configuration and maintenance module 226. The system software set 200 thus includes the modules that may be used to implement a single ultrasound diagnostic system. Certain modules may operate independently of other modules. Some software modules, however, may pass intermediate results or partially processed data to other software modules via the communication links 166 for further processing. The software modules noted above are exemplary only. In other words, additional software modules may be added for other any other tasks to be performed by a given medical diagnostic systems, such as an external communication module (e.g., email transmission and reception), or a specific type of diagnostic module (e.g., a diagnostic module for the INSIGHT project).

The system operation module 202 carries out system control functions. As examples, the 202 may directly control the electromechanical subsystem 102 to drive motor servos, evaluate sensor feedback, and initiate and terminate an ultrasound imaging sequence. To this end, in one implementation, the system operation computer 110 couples directly to the electromechanical subsystem 102 to accomplish system operation tasks.

The report module 204 executes patient reporting functions. The patient reporting functions may include, for example, querying of patient images from the archiving module 206, and preparation, display, and printing of patient examination records, billing records, and patient contact information.

The archiving module 206 is responsible for maintaining database records related to the operation of the diagnostic system. The database records may include patient examination images (either static images or image sequences (e.g., MPEG2 or other compressed or non-compressed movies)), operation and maintenance statistics (e.g., the time, date, and examination type for each use of the diagnostic system, and its service history), patient contact, billing, and examination records, including physician diagnoses, and the like.

The image-processing module 208 is responsible for tasks associated with manipulation of images (still or video) generated by the diagnostic system. Thus, as examples, the image-processing module may provide image contrast enhancement, image cropping, resolution enhancement, and other image processing functions. The image-processing module 208 typically allows the operator to retrieve, examine, modify, print, and save processed images, for example, by communicating with the database maintained by the archiving module 206. The image-processing module may also perform volume rendering to construct 3-dimensional models from a series of 2-dimensional B-mode or Doppler data sets of images using known volume rendering techniques.

The beamforming module 210 is responsible, for example, for controlling beamforming required to generate images in an ultrasound imaging system. Thus, the beamforming module 210 may receive raw data representing ultrasound echo information, apply the appropriate steering and gain corrections to the raw data, and output processed data sets ready for scan conversion for display.

The scanning module 212 handles user interface events received from the user interface module 216, determines the mode of an ultrasound scan to be taken, and passes the appropriate scan parameters to the acquisition module 214. The acquisition module 214 handles requests for scan parameter changes, implements the scan parameter changes, and translates scan parameters if required by the hardware with the ultrasound scanner 108. The acquisition module 214 executes scan sequences in the operator selected manner, and transfers hardware events (e.g., overpower, scanner disconnect, and the like), for example, to the system operation module 202 for error handling. The acquisition module 214 also receives ultrasound data sets that have been collected and formed by the beamforming module 210 and relays the data sets to the presentation module 222.

The user interface module 216 implements, preferably, user menus in a windowed environment, displays scan parameters, and monitors operator interface hardware, including keyboard control panels and trackballs. The user interface module 216 also displays images and delegates menu events, keyboard panel events, and trackball events to the scanning module 212 and other modules.

The signal-processing module 218 performs signals processing of data sets acquired from the electromechanical subsystem 102 based upon the current mode of operation. The signal-processing module 218 may, for example, perform vector processing, including Doppler and Color Flow processing on the data sets.

The scan conversion module 220 converts data between coordinate systems. Thus, for example, the scan conversion module 220 may convert data sets in the polar coordinate system to the Cartesian coordinate system for ready display on a typical video monitor.

The presentation module 222 processes and displays ultrasound image information, including static images, video images, traces, and the like. The presentation module 222 is preferably adapted to display, additionally, Doppler and Color Flow images.

The measurement and analysis (M&A) module 224 provides an interface that allows the operator to examine the data returned during patient examination. As one example, the M&A module may allow the operator to determine blood flow velocity, perform volume measurements, perform 2-dimensional measurements such as determining cross sectional area and blood vessel diameter, perform cardiology or radiology analyses (e.g., locating of heart defects or tumors), and the like.

The diagnostic system configuration and maintenance (C&M) module 226 is responsible for interfacing with the archiving module 206 to track maintenance history for the diagnostic system. Thus, for example, the C&M module 226 preferably allows a technician to enter the results of routine or non-routine maintenance calls, allow operators to submit maintenance requests, and the like. The C&M module also allows an operator to perform initial setup and configuration operations on the diagnostic system (e.g., the number and type of scanners 108 and the type of interface provided to the communication links 166).

The system software set 200 implements any desired medical diagnostic system. In a preferred implementation, the system software set 200 implements an ultrasound system, and therefore includes modules specifically directed to ultrasound imaging, for example, the beamforming module 210, scanning module 212, and scan conversion module 220. The system software set (and electromechanical subsystem 102) differs between diagnostic systems, however. As one example, an X-ray imaging system may include a linear tomographic scan control module, rather than a beamforming module, and a servo motor system used to move an X-ray source. Thus, although the present discussion proceeds primarily with reference to the particular ultrasound system software set 200, it is noted that any other system software set may be used by determining which functions to include in the system software set for a given diagnostic system, dividing the system software set into software modules, and determining a distribution of the software modules to separate computers. The separation between computers may manifest itself, for example, as physically different computers connected by the communication links 166 (whether in the same room or miles apart), or as physically distinct computer systems located, for example, in a single multiple slot hardware chassis and dedicated to execute one or more particular software modules.

Each software module is preferably distributed to a computer that is optimized to execute that particular software module. More than one module may be distributed to a single computer, and a single module may be installed on multiple computers. As an example, returning to FIG. 1, the system operation module 124 executes on the system computer 110. The system computer 110 is particularly adapted to execute the system operation module 124, as an example, because the system computer 110 includes the requisite sensor and servo motor interfaces 120 that directly control the electromechanical subsystem 102. Additional software modules may reside on the system computer 100, however, including, for example, the scanning module 212, acquisition module 214, and user interface module 216.

The report computer 112 is also adapted for execution of its report software module 132. To this end the report computer 112 includes an ergonomic user interface 134 (e.g., a low emission monitor, a split keyboard, hand and wrist rests, and the like), a large screen monitor 136 (e.g., a 19 inch monitor for viewing patient records), and a high speed printer 138 (for quickly printing extensive reports).

Similarly, the archiving computer 114 is adapted to its role of executing the archiving software module 146. As noted above, one primary role of the archiving computer 114 is to maintain database records on all aspects of the diagnostic system and its patients. The archiving computer 114 may therefore include, for example, a high capacity disk (e.g., hundreds of Gigabytes or multiple Terabytes of storage) and high speed I/O subsystem (e.g., SCSI-3 20–40 MB/sec throughput) 148, a Redundant Array of Inexpensive Disks (RAID) 150, for reliability, and a high capacity removable media drive 152 (e.g., a rewriteable CDROM, or, preferably, a Magneto optical disk), useful for storing large image and movie files.

With respect to the imaging computer 116, it too is specifically adapted to provide the services offered by the image and video processing software module 160. Thus, as examples, the imaging computer 116 provides a user-friendly GUI 164 adapted to present image processing operation selections and a large screen, high resolution, high refresh rate monitor (e.g., 1280×1024, 75 Hz refresh) for detailed image viewing. Because the imaging computer 116 will execute sophisticated image processing algorithms, it preferably includes one or more high performance CPU subsystem 154 and a high capacity (e.g., 128 MB, 256 MB, or greater) memory 158. The CPU subsystems 154, may, for example, be built from high speed RISC or CISC processors, Symmetric Multiprocessing CPUs and operating systems, and the like. In alternate embodiments, the imaging computer 116 may incorporate a hardware or software MPEG video encoder or decoder for producing and editing movies that show, for example, blood flow or heartbeats.

Figure 3:
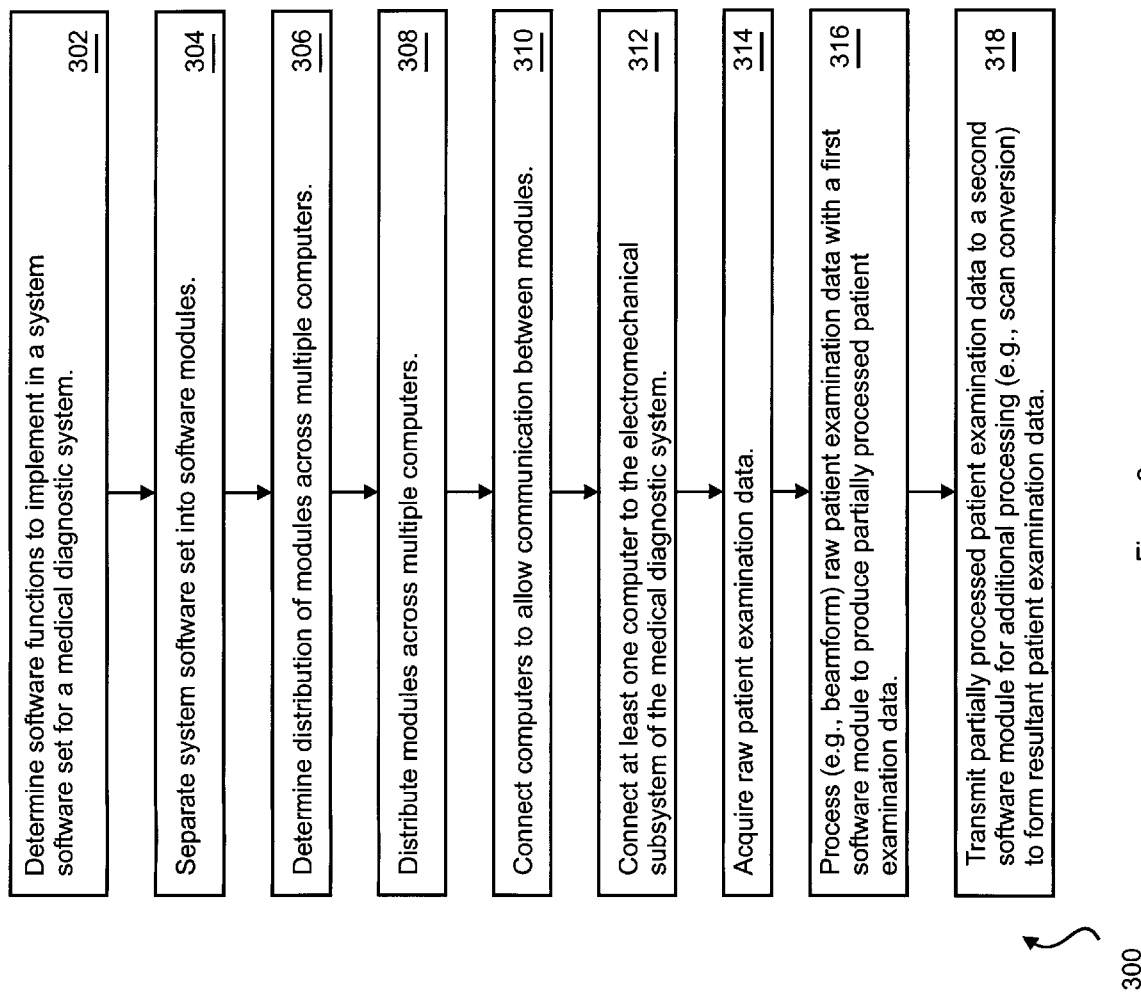
FIG. 3 shows a flow diagram for a method of implementing a distributed medical diagnostic system.

Turning now to FIG. 3, that figure shows a flow diagram 300 of a method for implementing a distributed medical diagnostic system. At step 302, the software functions to implement (e.g., those shown in FIG. 2) in a system software set are determined for a given medical diagnostic system. At step 304, the system software set is divided into software modules and a determination is made at step 306 as to a distribution of the software modules to computers. The software modules are then distributed to individual computers preferably optimized for the software modules at step 308. The computers are connected together at step 310 to allow the modules to interact, communicate, and share data. At least one computer, at step 312, is then connected to an electromechanical subsystem 102 of the medical diagnostic system to allow basic control over the medical diagnostic system.

At step 314, the distributed diagnostic system proceeds to acquire raw patient examination data. A first medical diagnostic software module processes the raw patient examination data (step 316) to form partially processed patient data. The first medical diagnostic software module then transmits the partially processed patient data over a communication link to a second medical diagnostic software module remotely located from the first medical diagnostic software module which forms resultant patient examination data (step 318). As described above, the first and second medical diagnostic software modules are selected from a system software set to implement a single medical diagnostic system. The partially processed patient data may be, for example, beamformed data, while the resultant patient examination data result, for example, from scan conversion, Doppler analysis, or image processing of the partially processed patient data.

The software modules and the computers exchange data over the communication links 166 and act in concert as a single medical diagnostic system. In this respect, the present distributed medical diagnostic system differs from multiple independently operable diagnostic systems simply linked together. In other words, the medical diagnostic system no longer resides on a single computer, but uses two or more computers distributed around a network of computers adapted to each software function to implement a single medical diagnostic system. The present distributed medical diagnostic system thereby allows a system designer to enhance the performance of a medical diagnostic system by adapting computer hardware to executed software modules. The present distributed medical diagnostic system allows a technician or system operator to perform hardware maintenance or hardware and software upgrades without taking down the entire medical diagnostic system, and further allows multiple doctors, technicians, or support personnel to use a single medical diagnostic system at the same time. Thus, a secretary may run a patient report while a doctor captures an ultrasound image and a second doctor processes ultrasound images at an image-processing computer. Note also that the architecture described above allows more than one instance of a software module at the same time in one system software set. For example, two secretaries may be connected to the same diagnostic system, each secretary using a different instance of the same software module, and both secretaries inserting new patients for the procedures to be performed today or in the future.

In general, it is noted that the sequence of generating or acquiring the patient examination data or other medical information is dependent on the type of medical diagnostic system, the application of the medial diagnostic system, and the particular procedure applied to the patient. Thus, the method of operation of the distributed medical diagnostic system may vary from one distributed diagnostic system (as implemented through its system software set) to another distributed diagnostic system (as implemented through what may be a very different system software set) due to the optimization that results in any given implementation of a distribution distributed diagnostic system.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. As an example, while the description above generally indicates that the software modules reside on different computers, the portions or subroutines of the software modules may also be distributed over the Internet (or other network) and therefore not bound or executed by a single computer. Furthermore, the software modules may be downloaded from a remote location, used from a remote node (which actually executes the software module), or be executed in multiple instances at multiple computers. There is also no requirement that each software module be able to communicate with ever other software module (e.g., the report module 204 may not need to communicate with the beamforming module 210), and thus some software modules in the system software set 200 may operate independently of other software modules. It is therefore intended that the invention not be limited to the particular embodiment disclosed, but that the invention include all embodiments falling within the scope of the appended claims.

What is claimed is:

1. A distributed medical diagnostic system comprising:
    a first computer executing a first medical diagnostic system software module;
    a second computer separate from the first computer, the second computer executing a second medical diagnostic system software module;
    a first communication interface in the first computer in communication with a second communication interface in the second computer, the first and second communication interfaces providing communication capability between the first and second medical diagnostic system software modules; and
    wherein the first and second medical diagnostic system software modules are different medical software system diagnostic modules and are members of a system software set to implement a predetermined medical diagnostic system.

2. The medical diagnostic system of claim 1, wherein the medical diagnostic system is one of an ultrasound imaging system, Magnetic Resonance Imaging system, and an X-ray imaging system.

3. The medical diagnostic system of claim 2, wherein the system software set comprises a system operation module and an image-processing module.

4. The medical diagnostic system of claim 3, wherein the set of system software further comprises an archiving module and at least one of a report module, volume rendering module, beamforming module, scanning module, acquisition module, user interface module, signal processing module, scan conversion module, and presentation module.

5. The medical diagnostic system of claim 2, wherein the first computer is primarily adapted for execution of the first medical diagnostic system software module.

6. The medical diagnostic system of claim 5, wherein the first medical diagnostic system software module is an image processing software module, and the first computer is adapted for image processing functions.

7. The medical diagnostic system of claim 6, wherein the first computer is adapted for image processing functions by providing at least one of a large screen monitor, high capacity image memory, parallel processing system, and image processing graphical user interface.

8. The medical diagnostic system of claim 5, wherein the first medical diagnostic system software module is a system operation module for the medical diagnostic system, and the first computer is adapted for control over the electromechanical subsystem of the medical diagnostic system separate from the first computer system.

9. The medical diagnostic system of claim 8, wherein the first computer is adapted for control over the electromechanical subsystem of the medical diagnostic system by providing an interface to control at least one of feedback sensors, servo motors, or digital x-ray detector readout.

10. The medical diagnostic system of claim 5, wherein the first medical diagnostic system software module is a report module for the medical diagnostic system, and the first computer is adapted for generating at least one of patient, maintenance, and operational reports for the medical diagnostic system.

11. The medical diagnostic system of claim 10, wherein the first computer is adapted for generating at least one of patient, maintenance, and operational reports by providing at least one of a high speed printer interface, ergonomic user interface, and a large screen monitor.

12. The medical diagnostic system of claim 5, wherein the first medical diagnostic system software module is an archiving module for the medical diagnostic system, and the first computer is adapted for storing at least one of patient, maintenance, and operational records for the medical diagnostic system.

13. The medical diagnostic system of claim 12, wherein the first computer is adapted for storing at least one of patient, maintenance, and operational records by providing at least one of a high capacity disk drive, high capacity removable media disk drive, and a redundant disk array.

14. The medical diagnostic system of claim 1, wherein the communication link is selected from the group consisting of serial, parallel, token ring, TCP/IP, and ATM protocol communication links.

15. The medical diagnostic system of claim 1, wherein the first medical diagnostic system software module processes data subsequently transmitted to the second medical diagnostic system software module for additional processing.

16. A method for implementing a distributed medical diagnostic system, the method comprising:
- separating a system software set for a predetermined medical diagnostic system into software modules;
- distributing different software modules among at least first and second separate computers;
- connecting the first and second computers through a first communication interface associated with the first computer and a second communication interface associated with the second computer; and
- connecting the first computer to an electromechanical subsystem of the predetermined medical diagnostic system.

17. The method of claim 16, further comprising the step of determining an allocation of the software modules to the first and second computers, and wherein the step of distributing comprises distributing in accordance with the allocation.

18. The method of claim 16, wherein the step of separating comprises separating the system software into at least a system operation module and an image processing module.

19. The method of claim 18, wherein the step of separating further comprises separating the system software into at least a report module and an archiving module.

20. The method of claim 18, wherein the step of distributing comprises distributing the system software module to the first computer, optimized for execution of the system software module with at least one of a sensor interface, or a servo motor controller, and distributing the image processing software module to the second computer, optimized for the image processing software module with at least one of a large screen monitor, high capacity image memory, high speed processing subsystem, and image processing graphical user interface.

21. The method of claim 16, wherein the step of distributing comprises distributing a first software module to the first computer, optimized for the first software module, and distributing a second software module to the second computer, optimized for the second software module.

22. A distributed medical diagnostic ultrasound system comprising:
- a first computer executing a first ultrasound system software module;
- a second computer separate from the first computer, the second computer executing a second ultrasound system software module, the second ultrasound system software module being different than the first ultrasound system software module;
- a first communication interface in the first computer in communication with a second communication interface in the second computer, the first and second communication interfaces providing communication capability between the first and second ultrasound system software modules; and
- an ultrasound electromechanical subsystem coupled to the communication interface.

23. The medical diagnostic system of claim 22, wherein the ultrasound electromechanical subsystem includes an acoustic power unit coupled to an ultrasound scanner.

24. The medical diagnostic system of claim 22 wherein the first ultrasound system software module and the second ultrasound system software module are selected from a predetermined ultrasound system software set.

25. The medical diagnostic system of claim 24 wherein the ultrasound system software set comprises a beamforming module, a system operation module, a scanning module, a user interface module, and a presentation module.

26. The medical diagnostic system of claim 25 wherein the ultrasound system software set further comprises a report module, an archiving module, and an image processing module.

27. The medical diagnostic system of claim 25 wherein the ultrasound system software set further comprises a measurement and analysis module.

28. The medical diagnostic system of claim 25 wherein the ultrasound system software set further comprises a configuration and maintenance module.

29. The medical diagnostic system of claim 25 wherein the first ultrasound system software module is a system operation module, and wherein the first computer is specifically adapted to execute the system operation module.

30. The medical diagnostic system of claim 26 wherein the second ultrasound system software module is an image processing module, and wherein the second computer is specifically adapted to execute the image processing module by providing at least one of a large screen monitor, high capacity image memory, parallel processing system, and image processing graphical user interface.

31. A method of operating a distributed medial diagnostic system, the method comprising:
- acquiring raw patient examination data;
- processing the raw patient examination data in accordance with a first medical diagnostic software module to form partially processed patient examination data;
- transmitting the partially processed patient examination data over a communication link to a second medical diagnostic software module remotely located from the first medical diagnostic software module, wherein the first and second medical diagnostic software modules are different medical software system diagnostic modules and are selected from a system software set to implement a single medical diagnostic system; and
- processing the partially processed patient examination data with the second medical diagnostic software module to form resultant patient examination data.

32. A method according to claim 31, wherein the step of processing the raw patient examination data comprises beamforming the raw patient examination data.

33. A method according to claim 31, wherein the step of processing the partially processed patient examination data comprises at least one of Doppler processing, archiving, scan converting, image processing, and measurement and analysis processing the partially processed patient examination data.

34. A method according to claim 32, wherein the step of processing the partially processed patient examination data comprises at least one of Doppler processing, archiving, scan converting, image processing, and measurement and analysis processing the partially processed patient examination data, and wherein the medical diagnostic system is an ultrasound system.

* * * * *